(12) United States Patent
Simmons et al.

(10) Patent No.: US 11,457,947 B2
(45) Date of Patent: Oct. 4, 2022

(54) ENDOVASCULAR TRANSLATING SCORING MECHANISM UTILIZING MOTORIZED BLADE

(71) Applicant: C.R. Bard, Inc., Tempe, AZ (US)

(72) Inventors: Brandon Simmons, Tempe, AZ (US); Mark Nicholas Wright, Gilbert, AZ (US)

(73) Assignee: C.R. Bard, Inc., Franklin Lakes, NJ (US)

( * ) Notice: Subject to any disclaimer, the term of this patent is extended or adjusted under 35 U.S.C. 154(b) by 324 days.

(21) Appl. No.: 16/675,684

(22) Filed: Nov. 6, 2019

(65) Prior Publication Data

US 2021/0128192 A1 May 6, 2021

(51) Int. Cl.
*A61B 17/3207* (2006.01)
*A61B 17/00* (2006.01)

(52) U.S. Cl.
CPC .......... *A61B 17/320758* (2013.01); *A61B 2017/00292* (2013.01)

(58) Field of Classification Search
CPC ... A61B 17/14; A61B 17/147; A61B 17/3207; A61B 17/320758; A61B 2017/320766; A61B 2017/320775; A61B 2017/320791
See application file for complete search history.

(56) References Cited

U.S. PATENT DOCUMENTS

| | | | |
|---|---|---|---|
| 4,986,807 A | 1/1991 | Farr | |
| 5,059,203 A * | 10/1991 | Husted | ......... A61B 17/320758 606/159 |
| 8,597,318 B2 | 12/2013 | Ozinga et al. | |
| 8,714,427 B2 | 5/2014 | McClintock et al. | |
| 2002/0010483 A1* | 1/2002 | Follmer | ................. A61B 10/06 606/159 |
| 2007/0167966 A1* | 7/2007 | Simpson | ............ A61B 17/3211 606/180 |
| 2008/0004643 A1* | 1/2008 | To | .................. A61B 17/320783 606/159 |
| 2010/0082051 A1* | 4/2010 | Thorpe | .......... A61B 17/320758 606/159 |
| 2012/0046599 A1 | 2/2012 | Schoenle et al. | |
| 2016/0374717 A1* | 12/2016 | Steele | ............ A61B 17/320758 606/159 |

(Continued)

FOREIGN PATENT DOCUMENTS

CN 209153879 U 7/2019
CN 209220427 U 8/2019

OTHER PUBLICATIONS

Loschak et al. (Dec. 2013). Automated Pointing of Cardiac Imaging Catheters. IEEE International Conference on Robotics and Automation. doi:10.1109/ICRA.2013.6631410.

(Continued)

*Primary Examiner* — Tuan V Nguyen
(74) *Attorney, Agent, or Firm* — Dickinson Wright PLLC; Nicholas P. Coleman

(57) ABSTRACT

An apparatus for scoring and treating a lesion includes a catheter, a scoring device, in the form of a rotary scoring element, and a drive unit for displacing the rotary scoring element and slicing the lesion. The rotary scoring element is displaceable between a stowed position fully contained within the catheter and a deployed position partially projecting from the catheter.

23 Claims, 9 Drawing Sheets

(56) References Cited

U.S. PATENT DOCUMENTS

2017/0071624 A1\* 3/2017 McGuckin, Jr ..... A61M 1/0058
2017/0181789 A1 6/2017 Ding et al.
2017/0196628 A1 7/2017 Nagtegaal

OTHER PUBLICATIONS

Wolverine Coronary Cutting Balloon. (Feb. 2017). Boston Scientific. Retrieved from https://www.bostonscientific.com/content/dam/Manuals/US/current-rev-en/50482216-01A_Wolverine_eDFU_en-US_s.pdf.
English machine translation of CN209153879.
English machine translation of CN209220427.

\* cited by examiner

ENDOVASCULAR TRANSLATING SCORING MECHANISM UTILIZING MOTORIZED BLADE

TECHNICAL FIELD

This document generally relates to devices incorporating a scoring mechanism, in particular, endovascular devices incorporating a scoring mechanism to actively score calcified peripheral lesions and, more particularly to an apparatus used to treat lesions, including below the knee (BTK) lesions.

BACKGROUND

BTK lesions are often hard calcifications that are resistant to traditional plain old balloon angioplasty (POBA) balloons. The apparatus disclosed in this document is generally suited for actively cutting a vessel wall in a controlled manner, such as for slicing or scoring a lesion associated therewith. Further, the apparatus disclosed in this document is particularly suited for actively scoring BTK lesions to a specified depth to ensure optimal dilation and enhanced drug delivery to the diseased vessel. Advantageously, the apparatus is particularly useful in treating critical limb ischemia (CLI) patients where more effective dilation and drug delivery is needed to have a better effect on the calcified lesion.

SUMMARY

In accordance with the purposes and benefits described herein are some embodiments of a new and improved apparatus for actively scoring calcified lesions in a diseased vessel. That apparatus comprises a catheter, a housing, a scoring device and a drive unit. The catheter includes a longitudinal axis, a proximal end and a distal end. The housing is connected to the distal end of the catheter. The scoring device is provided in the housing. The scoring device includes a rotary scoring element adapted for rotation about a rotation axis perpendicular to the longitudinal axis of the catheter when in a deployed position. The drive unit functions to displace the rotary scoring element and slice a lesion when the rotary scoring element is in the deployed position.

In one or more of the many possible embodiments of the apparatus, the scoring device includes a guide track in the housing that is adapted to guide the rotary scoring element between a stowed position within the housing and the deployed position wherein the rotary scoring element at least partially projects from the housing.

In one or more of the many possible embodiments of the apparatus, the rotary scoring element rotates about a rotation shaft held in the guide track and extending along a transverse axis of the catheter and the housing.

In one or more of the many possible embodiments of the apparatus, the drive unit includes a drive motor and a flexible driveshaft connected to the drive motor. That drive motor may be held in in a handle connected to the proximal end of the catheter and the flexible driveshaft extends through a lumen of the catheter to the rotary scoring element. More particularly, the handle may include a slide actuator adapted to displace the rotary scoring element between the stowed position and the deployed position.

In one or more of the many possible embodiments of the apparatus, the drive motor is carried or mounted on a carriage within the handle and the carriage is displaceable along a guide element fixed to the handle between a first position wherein the rotary scoring element is in the stowed position and a second position wherein the rotary scoring element is in the deployed position. The guide element may comprise two opposed guide rails.

In one or more of the many possible embodiments, the carriage includes a slide actuator adapted to displace the carriage between the first position and the second position and the rotary scoring element between the stowed position and the deployed position.

In one or more of the many possible embodiments of the apparatus, the rotary scoring element is a circular blade.

In one or more of the many possible embodiments of the apparatus, the rotation axis of the rotary scoring element is displaced from a first position adjacent a centerline of the catheter when in the stowed position to a second position further removed from the centerline of the catheter when in the deployed position.

In one or more embodiments of the apparatus, the apparatus further includes a guidewire extending through the lumen of the catheter. That lumen may include a first section that receives the guidewire and a second section that receives the flexible driveshaft.

In one or more of the many possible embodiments of the apparatus, a yoke connects a free end of the driveshaft to the rotary scoring element and holds the rotary scoring element in the guide track. In such an embodiment, the drive motor is a linear motor that translates the driveshaft and the rotary scoring element in a back-and-forth motion. That back-and-forth motion is along or aligned with the longitudinal axis of the catheter.

In contrast, in one or more of the many possible embodiments, the drive unit further includes a transmission connecting the flexible driveshaft to the rotary scoring element. That transmission may comprise a worm drive. That worm drive may include a worm connected to the free end of the flexible driveshaft and a worm gear connected to the rotary scoring element. The apparatus may also include a yoke holding the rotary scoring element in the guide track. In such an embodiment, the transmission may be carried on the yoke.

In one or more of the many possible embodiments of the apparatus, an anchor element is provided on the housing. Such an anchor element is adapted to hold the housing in position within a vessel of a patient adjacent the lesion to be treated. The anchor element may be provided on the distal side of the scoring element, on the proximal side of the scoring element or on both the proximal and distal sides of the scoring element. The anchor element may comprise one or more inflatable balloons.

In one or more of the many possible embodiments of the apparatus, the apparatus may include a biasing element in the housing adapted to bias the rotary scoring element toward the stowed position. The biasing element may comprise a spring.

In accordance with yet another aspect, a method is provided for scoring a lesion in a diseased vessel. That method comprises the steps of: (a) positioning a scoring device carried on a catheter adjacent to the lesion; (b) deploying the scoring device for active scoring and (c) translating the scoring device back-and-forth by a linear motor to slice the lesion. The method may also include providing the back-and-forth motion along an active scoring line aligned with the longitudinal axis of the catheter.

In accordance with still another aspect, a method is provided for scoring a lesion in a diseased vessel comprising the steps of: (a) positioning a scoring device carried on a catheter adjacent the lesion, (b) deploying the scoring device for active scoring, and (c) rotating with a drive motor the scoring device about an axis of rotation transverse to the longitudinal axis of the catheter.

Such a method may further include the step of connecting the drive motor in a handle at a proximal end of the catheter to a transmission at a distal end of the catheter by a flexible driveshaft. Further, the method may include using a worm at an end of the flexible driveshaft engaged with a worm gear fixed to the scoring device to rotate the scoring device.

In the following description, there are shown and described several embodiments of the apparatus. As it should be realized, the apparatus is capable of other, different embodiments and its several details are capable of modification in various, obvious aspects all without departing from the apparatus as set forth and described in the claims. Accordingly, the drawings and descriptions should be regarded as illustrative rather than restrictive.

BRIEF DESCRIPTION OF THE DRAWING FIGURES

The accompanying drawing figures incorporated herein and forming a part of this patent specification, illustrate several aspects of the apparatus and together with the description serve to explain certain principles thereof.

FIG. 4 also illustrates the catheter within a diseased vessel and the deployed rotary scoring element scoring a lesion with a translating, linear back-and-forth motion.

Figure 1:
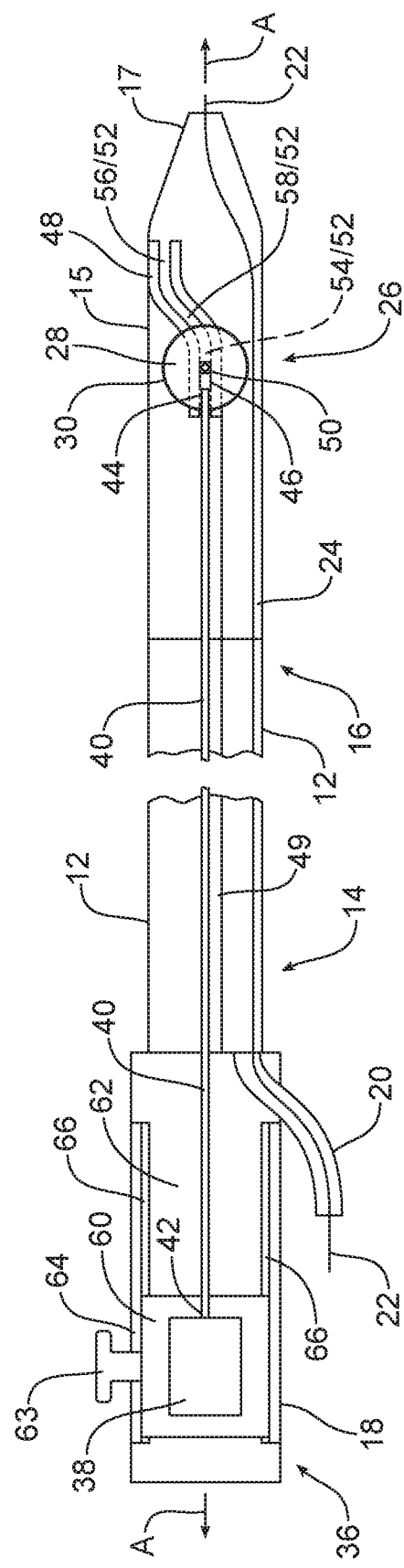
FIG. 1 is a cross sectional view of a first embodiment of the apparatus shown with the scoring device in the stowed position.

The drawings are not necessarily drawn proportionally or to scale. For example, the dimensions of some of the elements may be exaggerated relative to other elements for clarity or several physical components may be included in one functional block or element. Further, sometimes reference numerals may be repeated among the drawings to indicate corresponding or analogous elements.

DETAILED DESCRIPTION

In the following detailed description, numerous specific details are set forth to provide a thorough understanding of the disclosed concepts. Those of ordinary skill in the art will know that the disclosed inventions may be practiced without these specific details. In other instances, well-known methods, procedures, components, or structures may not have been described in detail so as not to obscure the disclosed inventions.

The description provided below and in regard to the figures applies to all embodiments unless noted otherwise, and features common to each embodiment are similarly shown and numbered.

Figure 2:
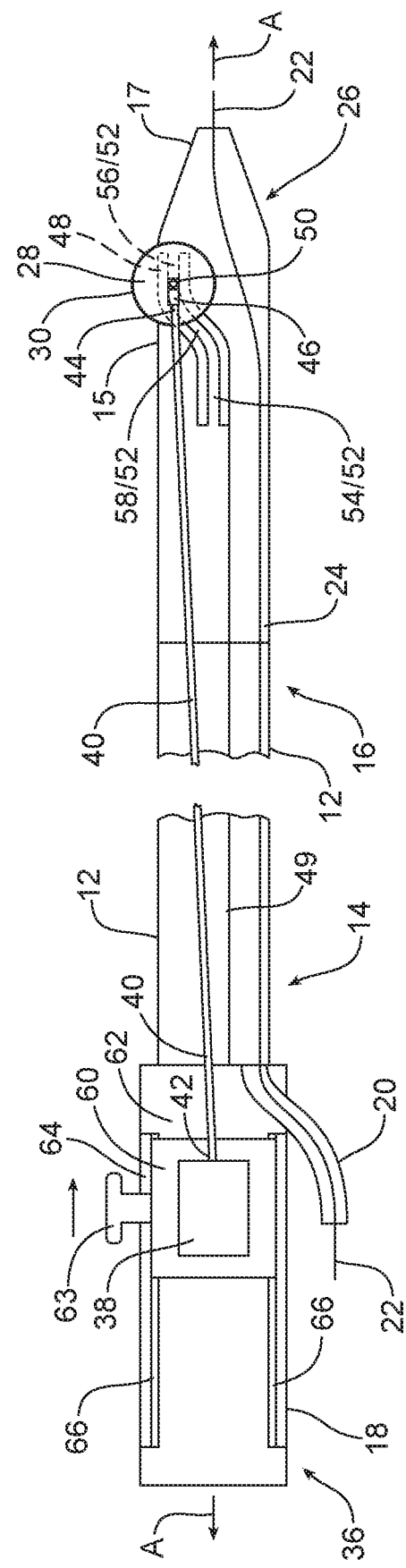
FIG. 2 is a view similar to FIG. 1 but showing the scoring device in the deployed position.

Reference is now made to FIGS. 1 and 2 which illustrate a first possible embodiment of the apparatus 10 used to score and treat lesions such as calcified lesions including below the knee (BTK) lesions. The apparatus 10 includes a catheter 12 comprising an elongated hollow body having a longitudinal axis A, a proximal end 14 and a distal end 16. The catheter may be made from an extruded polymer material (e.g. PEBAX® brand PEBA, Nylon, PET, etc.) which may or may not be braided or loaded with radioopaque materials. The catheter shaft may also be a stainless steel or nitinol hypotube with or without cuts to increase flexibility which may or may not be laminated with various types of plastic (PEBAX® brand PEBA, Nylon, PET, etc.). The catheter 12 may be of considerable length (e.g. 100-200 centimeters, or otherwise suitable to allow the housing 15 at the distal end 16 of the catheter to reach a treatment area of interest in the vasculature of a patient while the handle 18 connected to the proximal end 14 of the catheter remains accessible to the surgeon external to the vasculature.

As is known in the art, the handle 18 may include one or ports 20. As illustrated in FIG. 1, the port 20 receives a guidewire 22 that may pass through a guidewire lumen 24 in the body of the catheter. The guidewire 24 functions in a manner known in the art to help place the catheter 12 at the desired location within the vasculature where the apparatus 10 may be used to score and treat a lesion. For purposes of clarity of illustration of other structures, only a portion of the guidewire 24 is illustrated in FIG. 1 and in FIG. 2.

The handle 18 may be made from various types of plastic (ABS, polycarbonate, etc.) that may or may not be coated with a soft silicone grip. The handle 18 may be cylindrical in shape or contoured. The internal mechanisms of the handle 18, described below, may be made from various types of plastic (ABS, polycarbonate, etc.), stainless steel, or a combination thereof.

The housing 15 may be an extrusion of various types of plastic (PEBAX® brand PEBA, Nylon, PET, etc.) which may or may not be braided or loaded with radioopaque materials. The housing 15 may also be stainless steel or nitinol hypotube with or without cuts to increase flexibility and may or may not be laminated with various types of plastics (PEBAX® brand PEBA, Nylon, PET, etc.).

The tip 17 of the housing 15 may be tapered and may be an extrusion made from various types of plastic (PEBAX® brand PEBA, Nylon, PET, etc.) which may or may not be braided or loaded with radioopaque material. The tip 17 of the housing 15 and the body of the housing 15 may be extruded as one piece or made as separate components bonded together.

As further illustrated in FIGS. 1 and 2, the apparatus 10 also includes a scoring device, generally designated by reference numeral 26. In the illustrated embodiment, the scoring device comprises a rotary scoring element 28, such as a circular blade having a disc shape and serrations 30 along the continuous scoring edge. The rotary scoring element 28 may be made from any appropriate material including, for example, an appropriate plastic (ABS, polycarbonate, etc.) or metal (e.g. stainless steel) material and may be sharp or dull depending upon the desired treatment effect. Furthermore, the rotary scoring element 28 may be associated (e.g. coated) with a drug (e.g. Paclitaxel) for delivery to a vessel wall or lesion during the scoring process. In other embodiments, the rotary scoring element is free of serrations.

While a circular blade is illustrated in drawing FIGS. 1 and 2, the rotary scoring element 28 could assume another shape such as square, rectangular, contoured or notched. The rotary scoring element 28 may or may not be fully or partially laminated with various types of plastic (PEBAX® brand PEBA, Nylon, PET, etc.).

While the rotary scoring element 28 illustrated in the drawing figures comprises only one blade, it should be appreciated that it may alternatively comprise two, three, four or more blades.

The rotary scoring element 28 is oriented with the serrations 30 along the cutting edge aligned parallel to the longitudinal axis A of the catheter 12 and the housing 15 while the axis of rotation R of the rotary scoring element extends transversely across the housing: that is, substantially perpendicular to the longitudinal axis of the catheter and the housing.

As will become apparent from the following description, the rotary scoring element 28 is displaceable between; (a) a stowed position as illustrated in FIG. 1, wherein the entire rotary scoring element is held within the perimeter of the housing 15, and (b) a deployed position wherein the rotary scoring element projects at least partially through an opening 32 in the wall 34 of the housing. As should be appreciated, the stowed position allows placement of the catheter 12 and housing 15 in the diseased vessel without interference from the rotary scoring element which is fully contained within the housing while the deployed position allows the rotary scoring element to be used to score and treat a lesion.

A drive unit, generally designated by reference numeral 36 is adapted or configured for displacing the rotary scoring element 28 and slicing a lesion when the rotary scoring element is in the deployed position. As illustrated in FIGS. 1 and 2, the drive unit 36 includes a drive motor 38 and a semi-flexible or flexible driveshaft 40 that will bend with the catheter 12 but not kink in the catheter. A first end 42 of the driveshaft 40 is connected to the output shaft (not shown) of the drive motor 38. A second end 44 of the driveshaft 42 is connected to a shoe or yoke 46 that slides in a guide track 48 held in the housing 15 and adapted to guide the rotary scoring element 28 between the stowed and deployed positions.

Figure 3A:
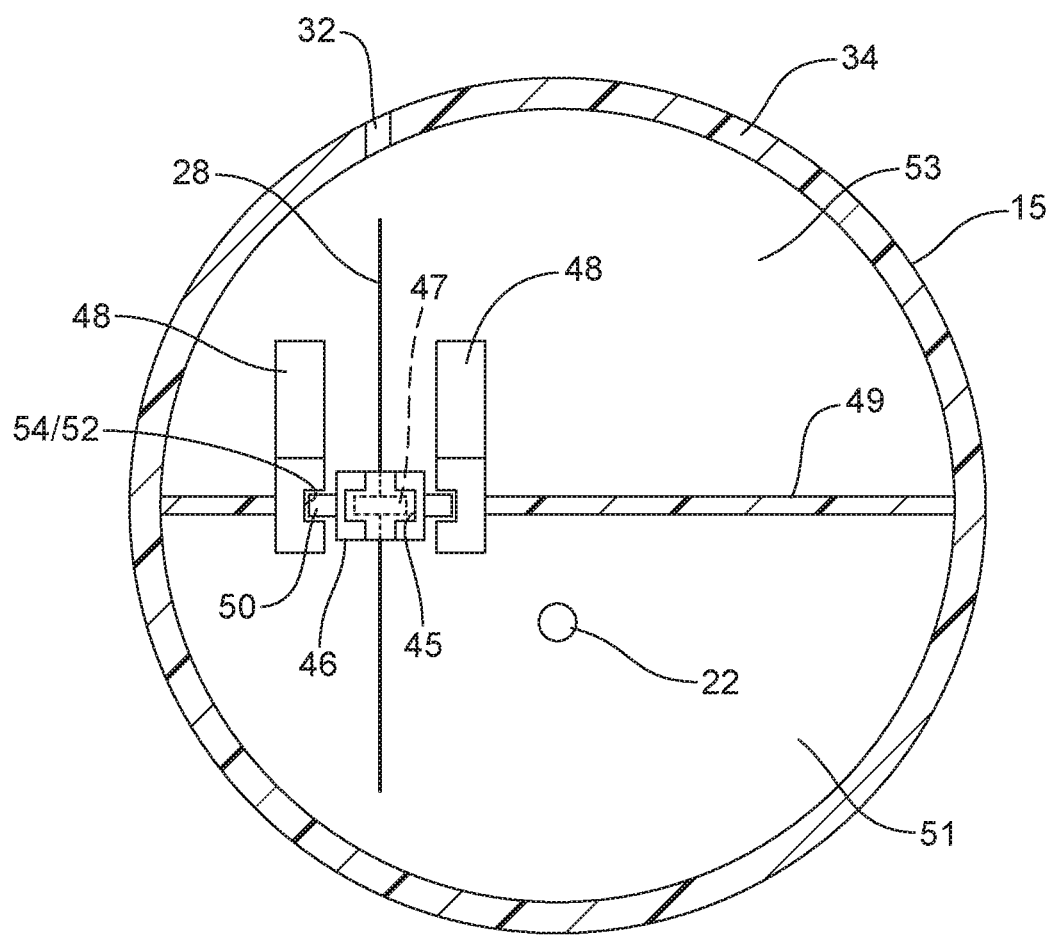
FIG. 3A is a transverse cross sectional view through the housing at the distal end of the catheter illustrating the rotary scoring device and the cooperating guide track for that device.

As illustrated in FIG. 3A, the guide track 48 is fixed to the partition 49 that divides the lumen of the catheter 12 and housing 15 into a first section 51 receiving the guidewire 22 and a second section 53 receiving the driveshaft 40. Other structural configurations are possible and anticipated by the following claims.

Figure 3B:
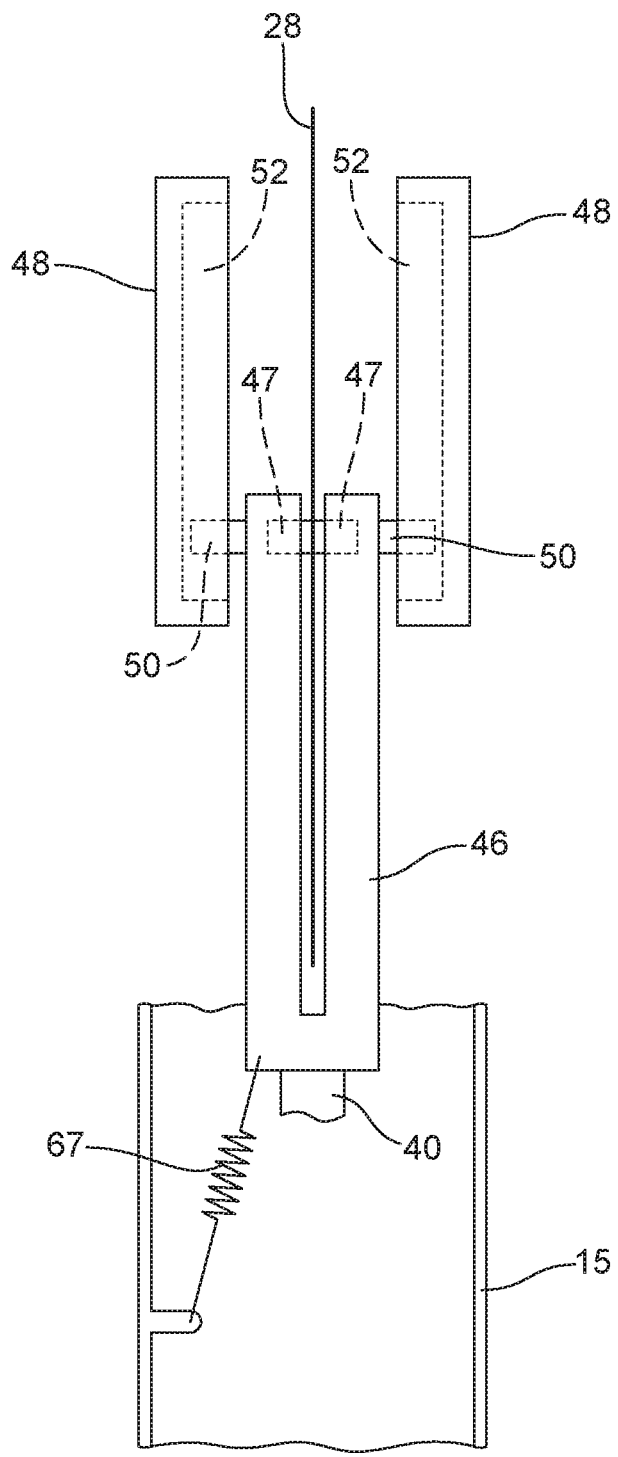
FIG. 3B is a detailed top plan view of the rotary scoring element held in the yoke.

More particularly as best shown in FIGS. 3A and 3B, the yoke 46 is u-shaped and includes opposed lugs 50 that are received and slide along opposed channels 52 in the guide track 48. The yoke 46 supports the rotary scoring element 28 by means of opposed sockets 45 that receive the rotation shaft 47 about which the rotary scoring element rotates. That rotation shaft 47 extends transversely across the housing 15 at an angle of approximately 90 degrees to the longitudinal axis A. See FIG. 3A. As illustrated in FIGS. 1 and 2, the guide track 48 and, more particularly, the channels 52 include a first section 54 adjacent the centerline and parallel to the longitudinal axis L of the catheter 12, a second section 56 adjacent the wall 34 that may be parallel to the longitudinal axis of the catheter and a sloped, transition section 58 that connects the first and second sections. The length of the second section 56 may be varied in order to adapt the apparatus 10 for making score lines of different lengths.

The yoke 46 and the guide track 48 may be made from any appropriate material including, for example, various types of plastics such as ABS, polycarbonate, etc., stainless steel or a combination thereof.

When the rotary scoring element 28 is in the stowed position, the opposed lugs 50 of the yoke 46 are received in the first section 54 (see FIG. 1). When the rotary scoring element 28 is in the deployed position, the opposed lugs 50 of the yoke 46 are received in the second section 56 (see FIG. 2). When the rotary scoring element 28 is being displaced between the stowed position illustrated in FIG. 1 and the deployed position illustrated in FIG. 2, the opposed lugs 50 of the yoke 46 are sliding along the sloped transition section 58. Here it should be appreciated that the rotation shaft 47 of the rotary scoring element 28 is displaced from a rest position adjacent the centerline of the catheter when the rotary scoring element is in the stowed position to an active scoring position further removed from the centerline of the catheter when the rotary scoring element is in the deployed position.

Figure 5:
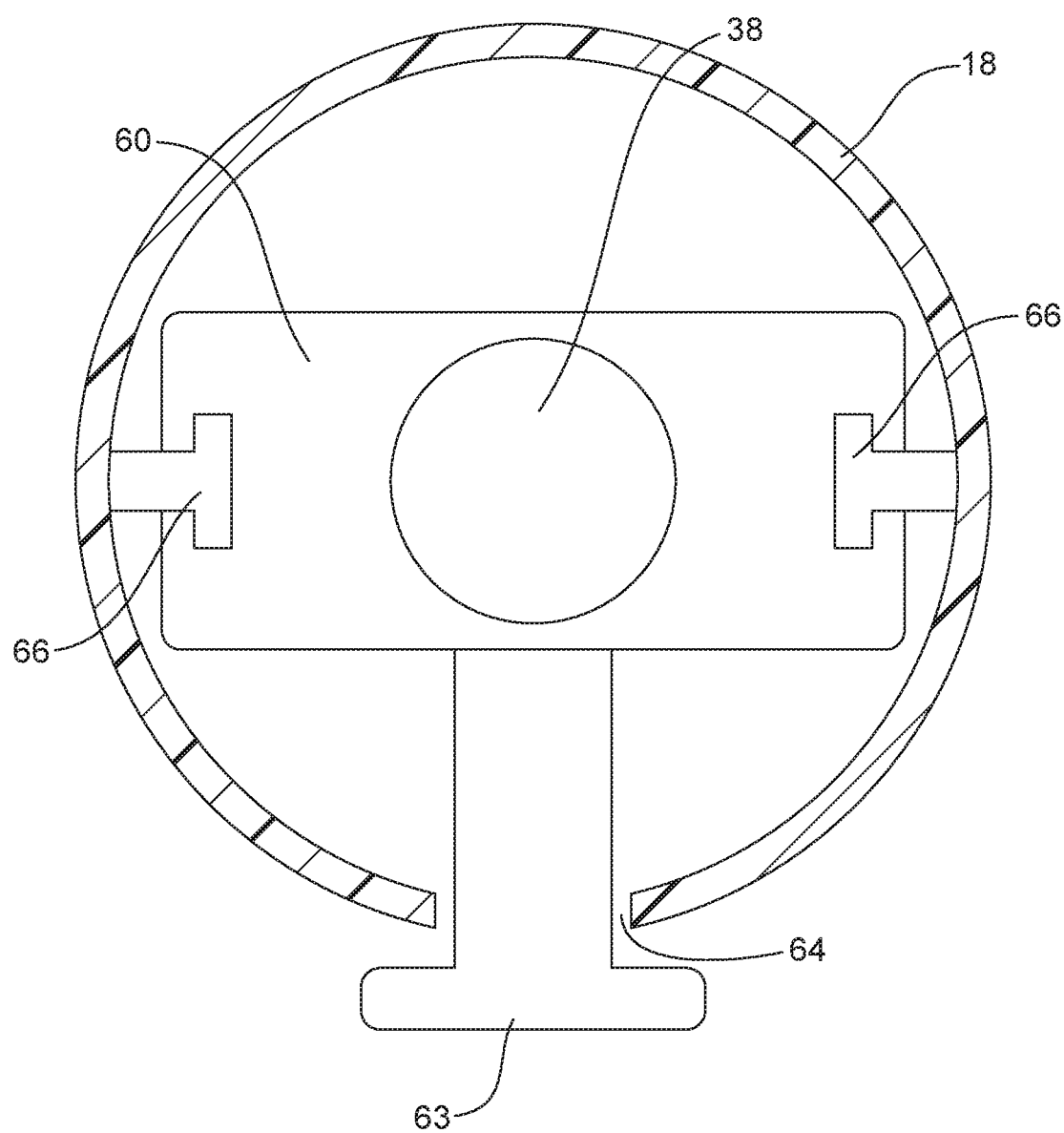
FIG. 5 is a detailed schematic transverse cross sectional view of the handle of the apparatus illustrating the drive motor held on a carriage that is displaced by a slide actuator between a first position and a second position.

The drive motor 38 is mounted on a carriage 60 held in an internal compartment 62 within the handle 18. See FIG. 5. A slide actuator 63 is connected at one end to the carriage 60 while the other end extends through an elongated slot 64 in the wall of the handle 18 so as to be accessible to the surgeon operating the apparatus 10. The carriage 60 is adapted to slide along the guide element, illustrated as opposed guide rails 66, connected to the handle 18 so as to be displaceable in a direction aligned with the longitudinal axis L of the catheter 12 between a first position at a first end of the handle as illustrated in FIG. 1 and a second position at a second end of the handle as illustrated in FIG. 2. More specifically, when the carriage 60 and drive motor 38 held thereon is in the first position, the rotary scoring element 28 is in the stowed position within the catheter 12 (See FIG. 1). In contrast, when the carriage 60 and the drive motor 38 held thereon is in the second position, the rotary scoring element 28 is in the deployed position illustrated in FIG. 2. In other words, the longitudinal displacement of the carriage 60 and drive motor 38 resulting from the lateral movement along the opposed guide rails 66 in the handle 18, functions, through lateral shifting of the driveshaft 40, to translate the rotary scoring element 28 along the guide track 48 between the stowed and deployed positions.

The slide actuator 63 illustrated in FIGS. 1 and 2 is a longitudinally translating or sliding mechanism. In other embodiments of the apparatus 10, the actuator may be an infinite control rotated threaded mechanism or a defined single turn mechanism with a gear drive. The slide could also be controlled manually by the user. In some embodiments of the apparatus 10, activation expands the rotary scoring element to a defined position projecting a defined distance beyond the wall of the housing 15. In other embodiments, that distance is adjustable by operation of the actuator 63 and resulting positioning of the yoke 46 and rotary scoring element 28 with respect to the guide track 48.

In one or more of the many possible embodiments of the apparatus 10, a biasing element 67 may be provided in the housing 15 to bias the yoke 46 and, therefore, the rotary scoring element 28 held in the yoke toward the stowed position where the rotary scoring element is fully contained within the housing. In FIG. 3B, the biasing element 67 is illustrated as a tension spring. In still other embodiments, a separate control wire (not shown) may be provided for this purpose.

Figure 4:
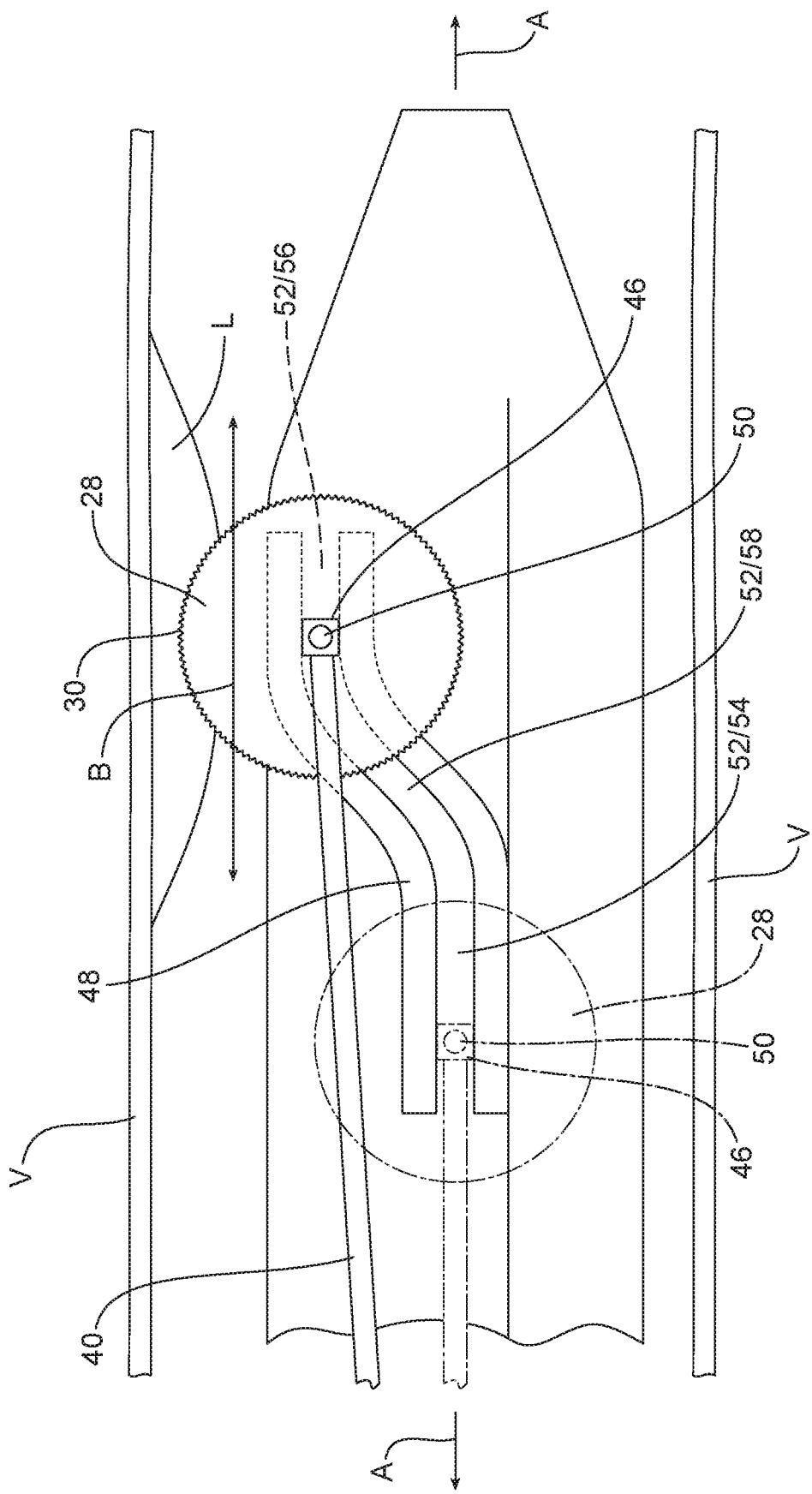
FIG. 4 is a detailed top plan view of the guide track in the housing that is adapted to guide the rotary scoring element between the stowed and deployed positions.

The catheter 12 is placed in the diseased vessel V using the guidewire 22 in a manner known in the art. During this placement, the rotary scoring element 28 is maintained in the stowed position within the housing 15. Once properly positioned at the lesion L to be treated, the rotary scoring element 28 is deployed by manipulation of the slide actuator 63 as illustrated in FIG. 4. The rotary scoring element 28 may then be used to score and treat the lesion L on the wall of the vessel V.

More particularly, in the embodiment illustrated in FIGS. 1 and 2, the drive motor 38 is a linear motor that translates the driveshaft 40 and the rotary scoring element 28 connected thereto through the yoke 46 back-and-forth in the direction of double action arrow B along and parallel to the longitudinal axis A of the catheter 12 and housing 15 to score a line across the lesion L. After the desired scoring and treatment of the lesion L is completed, the rotary scoring element 28 may be displaced back to the stowed position within the catheter 12 by operation of the slide actuator 63 and the catheter removed from the vessel V.

Figure 6:
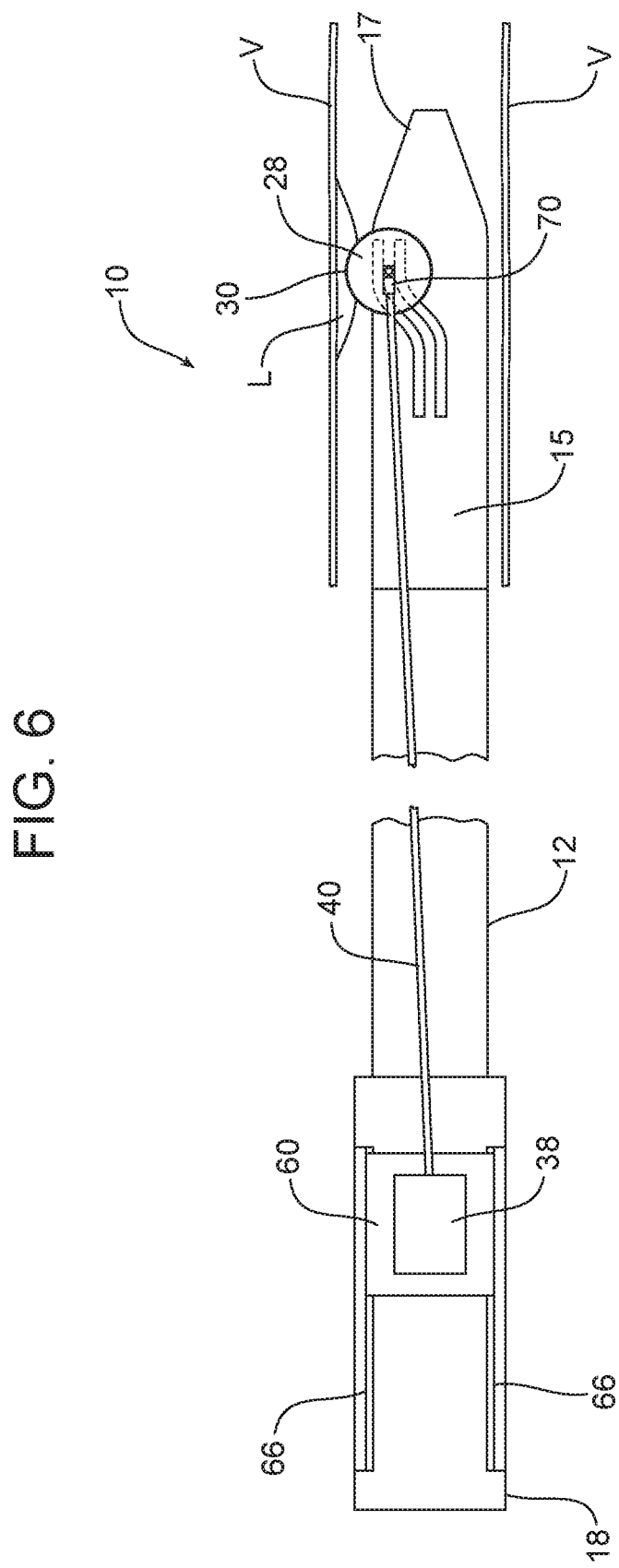
FIG. 6 is a schematic illustration of another possible embodiment of the apparatus incorporating a drive motor and a cooperating transmission that function to rotate the rotary scoring element in order to slice a lesion in a diseased vessel.
Figure 7:
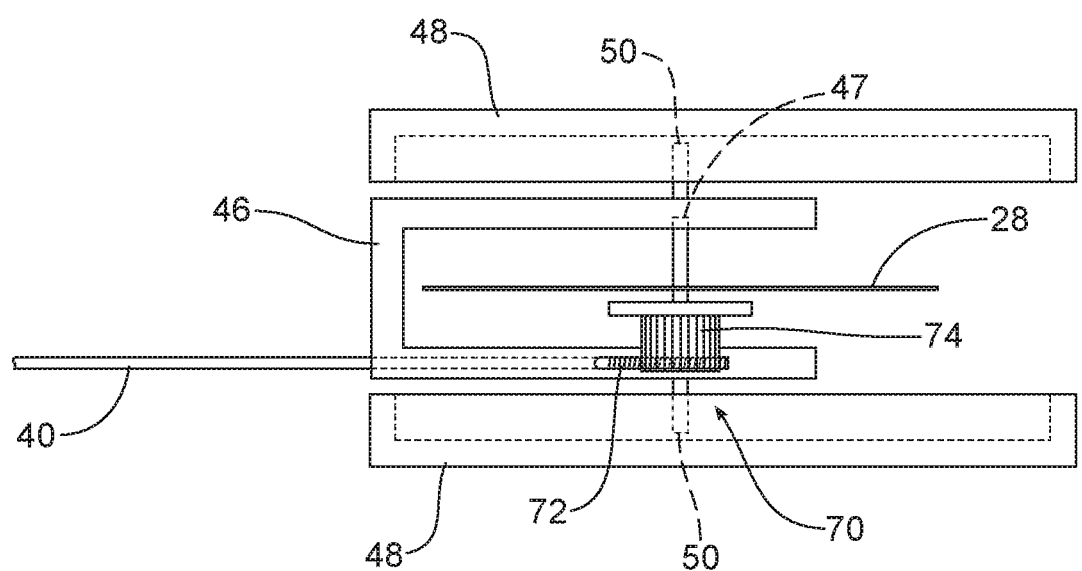
FIG. 7 is a detailed illustration of the worm drive connecting the driveshaft with the rotary scoring element.

In an alternative embodiment illustrated in FIGS. 6 and 7, when the rotary scoring element 28 is in the deployed position adjacent the lesion L, the drive motor 38 rotates the driveshaft 40 which is connected to the rotary scoring element 28 by a transmission 70. In the illustrated embodiment, that transmission 70 is a worm drive including a worm 72 connected to the distal end of the driveshaft 40 and a worm gear 74 connected to the rotary scoring element 28. Thus, when the drive motor 38 is activated, the driveshaft 40 is rotated which, in turn, rotates the worm 72 which, in turn, rotates the worm gear 74 and the rotary scoring element 28 that scores the lesion L. After treatment, the rotary scoring element 28 is displaced into the stowed position using the slide actuator 63.

In one or more possible embodiments of the apparatus 10, the apparatus may include an anchor element 80 on the housing 15 that is adapted or configured to hold the housing in a desired position in the vessel V of the patient adjacent the lesion L to be treated. That anchor element 80 may comprise an inflatable balloon that may be selectively inflated and expanded against the wall of the vessel V by delivering a fluid through a passageway (not shown) in the catheter 12 dedicated for this purpose in a manner known in the art. A dedicated port (not shown) on the handle 18 may feed fluid to that passageway.

Figure 8:
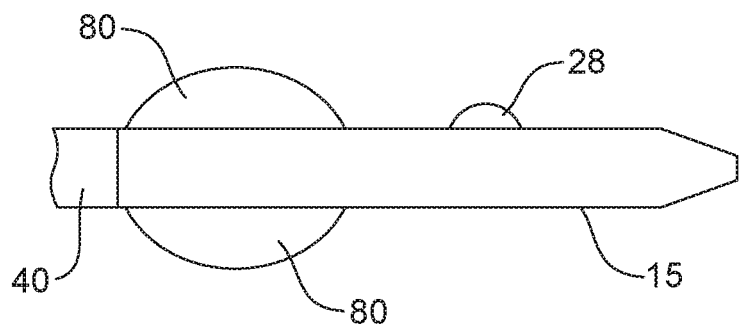
FIG. 8 is a schematic illustration of an embodiment of the apparatus including an anchor element on the housing at the proximal side of the rotary scoring element.
Figure 9:
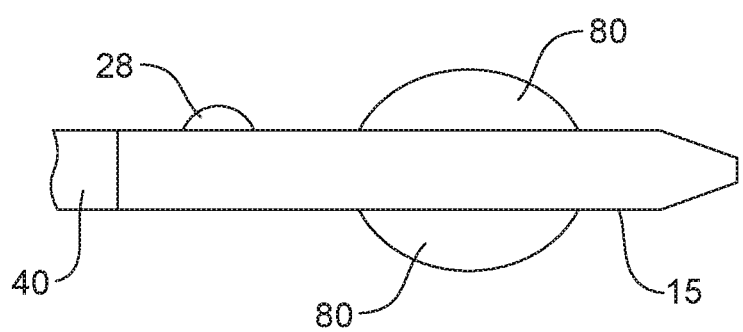
FIG. 9 is a schematic illustration of an embodiment of the apparatus including an anchor element on the housing at the distal side of the rotary scoring element.
Figure 10:
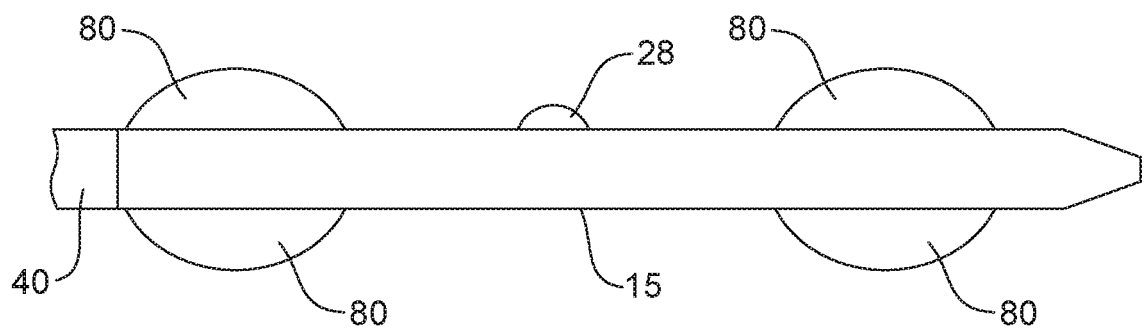
FIG. 10 is a schematic illustration of an embodiment of the apparatus including an anchor element on the housing at both the proximal and distal sides of the rotary scoring element.

As illustrated in FIG. 8, the anchor element 80 may be positioned proximal to the rotary scoring element 28. As illustrated in FIG. 9, the anchor element 80 may be positioned distal to the rotary scoring element 28. As illustrated in FIG. 10, the anchor element 80 comprises two inflatable balloons, one positioned proximal to the rotary scoring element 28 and one positioned distal to the rotary scoring element.

The inflatable balloon may be compliant or noncompliant and made from any appropriate material known in the art suitable for this purpose. The inflatable balloon may or may not be braided, may or may not include multiple layers of material and may or may not include reinforcing fibers.

This disclosure may be considered to relate to the following items:

1. An apparatus, comprising:
    a catheter having a longitudinal axis, a proximal end and a distal end;
    a housing connected to the distal end;
    a scoring device in the housing, said scoring device including a rotary scoring element adapted or configured for rotation about a rotation axis perpendicular to the longitudinal axis of said catheter when in a deployed position; and
    a driving unit for displacing said rotary scoring element for slicing a lesion when said rotary scoring element is in said deployed position.
2. The apparatus of item 1, wherein said scoring device includes a guide track, in the housing, adapted or configured to guide said rotary scoring element between a stowed position within the housing and the deployed position at least partially projecting from the housing.
3. The apparatus of item 2, the apparatus further comprising a rotation shaft held in the guide track and extending transversely across the housing, wherein the apparatus is configured such that the rotary scoring element is rotatable about the rotation shaft held in the guide track and extending transversely across the housing, and/or the rotary scoring element is configured to rotate about the rotation shaft held in the guide track and extending transversely across the housing.
4. The apparatus of any of the preceding items, wherein said drive unit includes a drive motor and a flexible driveshaft connected to said drive motor.
5. The apparatus of item 4, wherein the apparatus comprises a handle connected to the proximal end of the catheter, said drive motor in the handle connected to the proximal end of the catheter and/or said flexible driveshaft extends through a lumen of said catheter.
6. The apparatus of item 5, wherein the apparatus comprises a carriage in the handle and the drive motor is carried on the carriage in the handle.
7. The apparatus of item 6, further including a guide element fixed to the handle, optionally said carriage slidable along said guide element between a first position and a second position.
8. The apparatus of item 7, wherein the carriage includes a slide actuator adapted or configured to displace the carriage between the first position and the second position and/or the rotary scoring element between said stowed position and said deployed position.
9. The apparatus of any of the preceding items 2-8, wherein said guide element is or comprises opposed guide rails.
10. The apparatus of any of the preceding items, wherein said rotary scoring element is or comprises a circular blade.
11. The apparatus of any of the preceding items 3-10, wherein said rotation shaft is displaceable from a rest position, optionally adjacent a centerline of said catheter when in the stowed position to an active swing position, optionally further removed from said centerline of said catheter when in the deployed position.
12. The apparatus of any of the preceding items, further including a guidewire extending through a lumen of said catheter, optionally said lumen of the catheter of item 5.
13. The apparatus of item 12, wherein said lumen includes a first section receiving said guidewire and a second section for receiving said flexible driveshaft.

14. The apparatus of any of the preceding items if dependent from item 4, further including a yoke connecting a free end of the driveshaft to the rotary scoring element and holding said rotary scoring element in said guide track.
15. The apparatus of any of the preceding items if dependent from item 4, wherein said drive motor is a linear motor for translating said driveshaft and/or said rotary scoring element in a back-and-forth motion.
16. The apparatus of any of the preceding items if dependent from item 4, wherein said drive unit further includes a transmission connecting said flexible driveshaft to said rotary scoring element.
17. The apparatus of item 16, wherein said transmission is a worm drive.
18. The apparatus of item 17, wherein said worm drive includes a worm connected to said flexible driveshaft and a worm gear connected to said rotary scoring element.
19. The apparatus of any of the preceding items if dependent from item 2, further including a yoke holding said rotary scoring element in said guide track.
20. The apparatus of items 19 and 16, optionally also of items 17 and/or 18, wherein said transmission is carried on said yoke.
21. The apparatus of any of the preceding items, further including an anchor element on the housing, the anchor element holding the housing in position within a vessel of a patient adjacent the lesion.
22. The apparatus of item 21, wherein said anchor element is on a distal side of said rotary scoring element.
23. The apparatus of item 21, wherein said anchor element is on a proximal side of said rotary scoring element.
24. The apparatus of item 21, wherein said anchor element is on both a proximal side and a distal side of said rotary scoring element.
25. The apparatus of any of the preceding items if dependent from item 2, further including a biasing element for biasing the rotary scoring element toward the stowed position.
26. The apparatus of item 25, wherein the biasing element is a spring.
27. A method of scoring a lesion in a diseased vessel, comprising:
    positioning a scoring device carried on a catheter adjacent the lesion;
    deploying the scoring device for active scoring; and
    translating the scoring device back-and-forth by a linear motor to slice the lesion.
28. The method of item 27 including providing said back-and-forth motion along an active scoring line aligned with a longitudinal axis of the catheter.
29. A method of scoring a lesion in a diseased vessel, comprising:
    positioning a scoring device carried on a catheter adjacent the lesion;
    deploying the scoring device for active scoring; and
    rotating with a drive motor the scoring device about an axis of rotation transverse to a longitudinal axis of the catheter.
30. The method of item 29, including connecting the drive motor in a handle at a proximal end of the catheter to a transmission at a distal end of the catheter by a flexible driveshaft.
31. The method of item 30 including using a worm at an end of the driveshaft engaged with a worm gear fixed to the scoring device to rotate the scoring device.

Each of the following terms written in singular grammatical form: "a", "an", and the", as used herein, means "at least one", or "one or more". Use of the phrase One or more" herein does not alter this intended meaning of "a", "an", or "the". Accordingly, the terms "a", "an", and "the", as used herein, may also refer to, and encompass, a plurality of the stated entity or object, unless otherwise specifically defined or stated herein, or, unless the context clearly dictates otherwise. For example, the phrases: "a unit", "a device", "an assembly", "a mechanism", "a component, "an element", and "a step or procedure", as used herein, may also refer to, and encompass, a plurality of units, a plurality of devices, a plurality of assemblies, a plurality of mechanisms, a plurality of components, a plurality of elements, and, a plurality of steps or procedures, respectively.

Each of the following terms: "includes", "including", "has", "having", "comprises", and "comprising", and, their linguistic/grammatical variants, derivatives, or/and conjugates, as used herein, means "including, but not limited to", and is to be taken as specifying the stated component(s), feature(s), characteristic(s), parameter(s), integer(s), or step(s), and does not preclude addition of one or more additional component(s), feature(s), characteristic(s), parameter(s), integer(s), step(s), or groups thereof. Each of these terms is considered equivalent in meaning to the phrase "consisting essentially of." Each of the phrases "consisting of and "consists of, as used herein, means "including and limited to". The phrase "consisting essentially of means that the stated entity or item (system, system unit, system sub-unit device, assembly, sub-assembly, mechanism, structure, component element or, peripheral equipment utility, accessory, or material, method or process, step or procedure, sub-step or sub-procedure), which is an entirety or part of an exemplary embodiment of the disclosed invention, or/and which is used for implementing an exemplary embodiment of the disclosed invention, may include at least one additional feature or characteristic" being a system unit system sub-unit device, assembly, sub-assembly, mechanism, structure, component or element or, peripheral equipment utility, accessory, or material, step or procedure, sub-step or sub-procedure), but only if each such additional feature or characteristic" does not materially alter the basic novel and inventive characteristics or special technical features, of the claimed item.

The term "method", as used herein, refers to steps, procedures, manners, means, or/and techniques, for accomplishing a given task including, but not limited to, those steps, procedures, manners, means, or/and techniques, either known to, or readily developed from known steps, procedures, manners, means, or/and techniques, by practitioners in the relevant field(s) of the disclosed invention.

Terms of approximation, such as the terms about, substantially, approximately, etc., as used herein, refers to ±10% of the stated numerical value. Use of the terms parallel or perpendicular are meant to mean approximately meeting this condition, unless otherwise specified.

It is to be fully understood that certain aspects, characteristics, and features, of the invention, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the invention which are illustratively described and presented in combination or sub-combination in the context or format of a single embodiment may also be illustratively described and presented in the context or format of a plurality of separate embodiments.

Although the inventions of this disclosure have been illustratively described and presented by way of specific exemplary embodiments, and examples thereof, it is evident that many alternatives, modifications, or/and variations, thereof, will be apparent to those skilled in the art Accordingly, it is intended that all such alternatives, modifications, or/and variations, fall within the spirit of, and are encompassed by, the broad scope of the appended claims.

The foregoing has been presented for purposes of illustration and description. It is not intended to be exhaustive or to limit the embodiments to the precise form disclosed. Obvious modifications and variations are possible in light of the above teachings. For example, a strain relief of a type known in the art may be provided between the catheter 12 and the handle 18. The strain relief may be an extrusion of various types of plastic such as PEBAX® brand PEBA, Nylon, PET, etc. As another example, the shaft of the catheter 12 may include GeoAlign markings. As still another example, the drive motor 38 could be a reusable accessory that is connected to a disposable carriage 60. All such modifications and variations are within the scope of the appended claims when interpreted in accordance with the breadth to which they are fairly, legally and equitably entitled.

What is claimed:

1. An apparatus, comprising:
   a catheter having a longitudinal axis, a proximal end and a distal end;
   a housing connected to the distal end;
   a scoring device in the housing, said scoring device including
     a rotary scoring element adapted for rotation about a rotation shaft defining a rotation axis perpendicular to the longitudinal axis of said catheter when in a deployed position, and
     a guide track in the housing, said guide track adapted to hold the rotation shaft and to guide the rotary scoring element between a stowed position within the housing and the deployed position at least partially projecting from the housing;
   a driving unit for displacing said rotary scoring element and slicing a lesion when said rotary scoring element is in said deployed position, the driving unit including a drive motor and a flexible driveshaft connected to the drive motor; and
   a yoke connecting a free end of the driveshaft to the rotary scoring element and holding said rotary scoring element in said guide track.

2. The apparatus of claim 1, wherein said drive motor is held in a handle connected to the proximal end of the catheter and said flexible driveshaft extends through a lumen of said catheter.

3. The apparatus of claim 2, wherein the drive motor is carried on a carriage in the handle.

4. The apparatus of claim 3, further including a guide element fixed to the handle, said carriage sliding along said guide element between a first position and a second position.

5. The apparatus of claim 4, wherein the carriage includes a slide actuator adapted to displace the carriage between the first position and the second position and the rotary scoring element between said stowed position and said deployed position.

6. The apparatus of claim 5, wherein said guide element is opposed guide rails.

7. The apparatus of claim 5, wherein said rotary scoring element is a circular blade.

8. The apparatus of claim 5, wherein said rotation shaft is displaced from a rest position adjacent a centerline of said catheter when in the stowed position to an active swing position further removed from said centerline of said catheter when in the deployed position.

9. The apparatus of claim 2, further including a guidewire extending through said lumen of said catheter.

10. The apparatus of claim 9, wherein said lumen includes a first section receiving said guidewire and a second section receiving said flexible driveshaft.

11. The apparatus of claim 1, wherein said drive motor is a linear motor that translates said driveshaft and said rotary scoring element in a back-and-forth motion.

12. The apparatus of claim 1, wherein said drive unit further includes a transmission connecting said flexible driveshaft to said rotary scoring element.

13. The apparatus of claim 12, wherein said transmission is a worm drive.

14. The apparatus of claim 13, wherein said worm drive includes a worm connected to said flexible driveshaft and a worm gear connected to said rotary scoring element.

15. The apparatus of claim 12, wherein said transmission is carried on said yoke.

16. The apparatus of claim 1, further including an anchor element on the housing, the anchor element holding the housing in position within a vessel of a patient adjacent the lesion.

17. The apparatus of claim 16, wherein said anchor element is on a distal side of said rotary scoring element.

18. The apparatus of claim 16, wherein said anchor element is on a proximal side of said rotary scoring element.

19. The apparatus of claim 16, wherein said anchor element is on both a proximal side and a distal side of said rotary scoring element.

20. The apparatus of claim 1, further including a biasing element biasing the rotary scoring element toward the stowed position.

21. The apparatus of claim 20, wherein the biasing element is a spring.

22. An apparatus, comprising:
    a catheter having a longitudinal axis, a proximal end and a distal end;
    a housing connected to the distal end;
    a scoring device in the housing, said scoring device including
      a rotary scoring element adapted for rotation about a rotation axis perpendicular to the longitudinal axis of said catheter when in a deployed position, and
      a guide track adapted to guide the rotary scoring element between a stowed position within the housing and the deployed position;
    a driving unit for displacing said rotary scoring element and slicing a lesion when said rotary scoring element is in said deployed position; and
    a biasing element biasing the rotary scoring element toward the stowed position.

23. An apparatus, comprising:
    a catheter having a longitudinal axis, a proximal end and a distal end;
    a housing connected to the distal end;
    a scoring device including a rotary scoring element adapted for rotation about a rotation shaft, said rotation shaft defining a rotation axis perpendicular to the longitudinal axis of said catheter when the rotary scoring element is in a deployed position;
    a guide track in the housing;
    a yoke adapted to receive at least a portion of the rotation shaft and to hold the rotary scoring element in the guide track and to guide the rotary scoring element between a stowed position within the housing and the deployed position at least partially projecting from the housing; and a driving unit for displacing said rotary scoring element between the stowed position and the deployed position and for slicing a lesion when said rotary scoring element is in said deployed position.

\* \* \* \* \*